United States Patent [19]

Keller, Jr.

[11] Patent Number: 4,688,556

[45] Date of Patent: Aug. 25, 1987

[54] SPINAL MASSAGE AND EXERCISE DEIVCE

[76] Inventor: Moreau A. Keller, Jr., Rte. 1, Box 242, Milton, Del. 19968

[21] Appl. No.: 827,100

[22] Filed: Feb. 7, 1986

[51] Int. Cl.[4] ........................ A61H 15/00; A61F 5/00

[52] U.S. Cl. ........................................ 128/57; 128/69; 128/DIG. 20

[58] Field of Search .................. 128/57, 60, 62 R, 67, 128/DIG. 20, 69

[56] References Cited

U.S. PATENT DOCUMENTS

| | | | |
|---|---|---|---|
| 1,468,072 | 9/1923 | Ogle | 128/DIG. 20 |
| 1,572,794 | 2/1926 | Hamilton | 128/57 |
| 1,593,014 | 7/1926 | Bushmiller | 128/57 |
| 1,643,040 | 9/1927 | Wentz | 128/57 |
| 1,748,425 | 2/1930 | Odell | 128/57 |
| 1,748,762 | 2/1930 | Gilbert | 128/57 |
| 2,286,324 | 6/1942 | Wentz | 128/57 |
| 2,447,269 | 8/1948 | Myers | 128/57 |
| 2,819,714 | 1/1958 | London | 128/57 |
| 4,178,922 | 12/1974 | Curlee | 128/DIG. 20 |

FOREIGN PATENT DOCUMENTS

| | | | |
|---|---|---|---|
| 645391 | 6/1937 | Fed. Rep. of Germany | 128/62 R |
| 2323851 | 11/1974 | Fed. Rep. of Germany | 128/57 |
| 3,215,763 | 11/1983 | Fed. Rep. of Germany | 128/57 |
| 2477870 | 9/1981 | France | 128/57 |
| 1534013 | 11/1978 | United Kingdom | 128/57 |
| 572266 | 11/1975 | U.S.S.R. | 128/69 |

*Primary Examiner*—Edgar S. Burr
*Assistant Examiner*—Tonya Lamb
*Attorney, Agent, or Firm*—Brady, O'Boyle & Gates

[57] ABSTRACT

One or more yielding oblate spheroids rotatably held in a support frame can roll on a support surface while the user of the device in a prone position has his or her spine resting on the rolling oblate spheriod or spheroids which gently and effectively massage the spine. The device is propelled by the legs of the user and therefore provides exercise. The tapered ends of the massage elements are releasably socketed in cup elements held on rotational bearings of the support frame.

8 Claims, 5 Drawing Figures

SPINAL MASSAGE AND EXERCISE DEIVCE

BACKGROUND OF THE INVENTION

The present invention relates to a spinal massage and exercise device which can more effectively and gently massage the spinal column while affording significant exercise to the user of the device.

An object of the invention is to provide an improved spinal massage and exercise unit which is portable, simplified in construction, and therefore economical to manufacture, convenient to use anywhere a flat support surface is available, and versatile in the sense that the number of rotating support elements can be varied and their degrees of hardness can be individually varied.

More particularly, it is an object of the invention to provide a back massage unit having a simple support frame for one or more rotatably held oblate spheroids whose major axes extend across the axis of the spine during usage and which preferably, although not necessarily, are inflatable so that the pressure of the massage elements on the back and spine can be varied.

Another important object of the invention is to provide a back massage unit of the above-mentioned character in which the tapered ends of the yielding massage elements are removably held in cups which are rotatable on the support frame of the unit, thereby eliminating the need for any additional means of securing the massage elements to the support frame, the mounting arrangement for the massage elements rendering them self-aligning while rolling on a flat support surface, such as a floor.

Other features and advantages of the invention will become apparent to those skilled in the art during the course of the following description.

DETAILED DESCRIPTION

Figure 1:
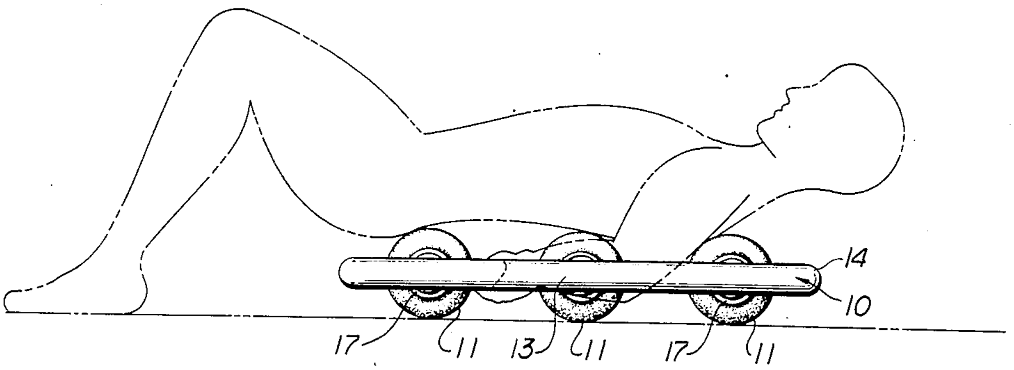
FIG. 1 is a side elevation of a spinal massage and exercise device according to the present invention.
Figure 2:
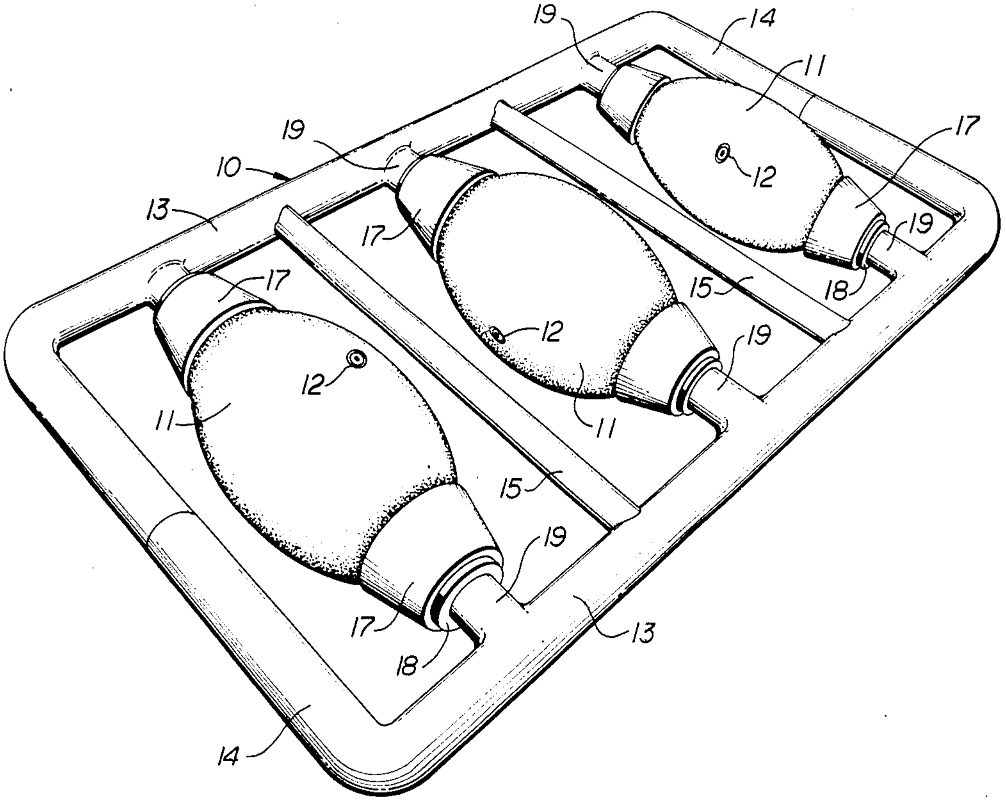
FIG. 2 is a perspective view of the device.
Figure 3:
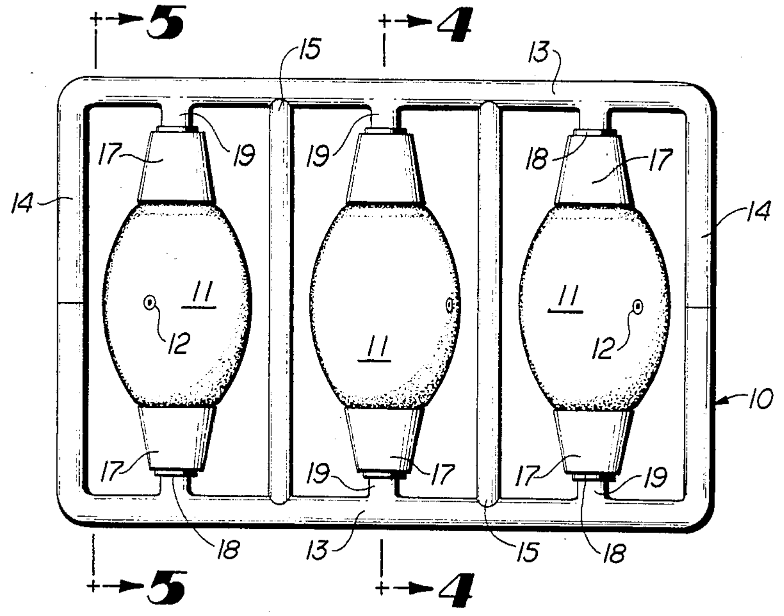
FIG. 3 is a plan view of the device.
Figure 4:
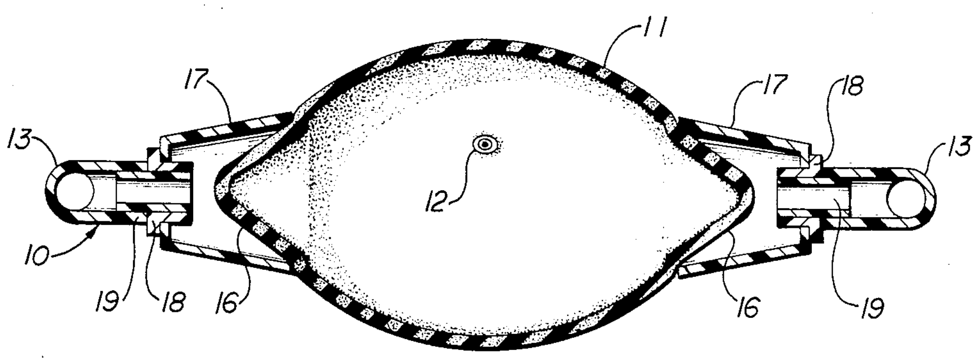
FIG. 4 is a transverse vertical section on an enlarged scale taken on line 4—4 of FIG. 3.

Referring to the drawings in detail wherein like numerals designate like parts, a spinal massage and exercise device according to the present invention comprises a substantially rigid generally rectangular support frame 10. The frame 10 can be constructed from any suitable sufficiently durable material, such as tough plastics material. The details of construction of the support frame 10 can vary, as long as a strong unitized frame is realized.

As shown in the drawings, a plurality of spinal massage elements 11 are rotatably held in the support frame 10. The massage elements are in the form of oblate spheroids and are preferably inflatable, although not necessarily so. If inflatable, the massage elements 11 are equipped with needle-inflating valves 12. The massage elements can be formed of rubber or rubber-like material, or, in some cases, they could be leather or the like, in which case they would be equipped with an inflation bladder. The advantage of making the massage elements 11 inflatable is that the degree of inflation of each massage element can be regulated, and thus the pressure exerted on the spine of the user can be regulated at each massage element or at some or all of them, if more than one massage element is utilized. While the drawings show three massage elements within the frame 10, it should be understood that the invention is not limited to this number and a greater or lesser number of massage elements can be used, or a single element only, if desired.

The massage elements 11 must be somewhat yielding in any case, and if solid non-inflatable elements are employed, their degree of hardness should be chosen so that an effective and comfortable spinal massage will be provided with no possibility of injuring the spine. Solid massage elements formed of rubber or rubber-like material can be utilized in some cases in lieu of the preferred inflatable elements.

The major axes of the elongated massage elements 11 extend transversely of the elongated frame 10 and perpendicular to its parallel longitudinal side bars 13. The elements 11 have their major axes in spaced parallel relationship on the frame 10 and the elements 11 are preferably equidistantly spaced and disposed between the end frame bars 14 and spaced parallel internal brace bars 15 of the frame 10. When properly inflated, or properly sized, if non-inflatable elements are utilized, the top and bottom rounded faces of the elements 11 project equidistantly above and below the support frame 10, which is disposed in a flat plane, as shown in the drawings.

The tapered end portions 16 of the yielding massage elements 11 are releasably held and socketed in cup elements 17, which are preferably somewhat conically tapered, as shown, but could be short straight cylindrical cups or tube sections, in some cases. The tapered end portions 16 project deeply into the cups 17 and are firmly held therein, although readily releasable therefrom at required times by applying sufficient hand pressure on the elements 11 at the proper locations. If the elements 11 are inflatable, the inflation pressure can be reduced somewhat to allow easy separation from the cups 17.

The outer ends of the cups 17 are held on coaxial bushings 18 which are journaled on transverse stub shafts 19 of the frame sides 13. The bushings 18 and stub shafts 19, being formed of plastics, constitute dry-lube bearings so that the massage elements 18 will turn freely on their longitudinal axes during use of the device. The resiliency of the massage elements, whether inflated or otherwise, exerts pressure on the cups 17 whereby the tapered end portions 16 are securely frictionally held in the cups 17 without slippage.

Figure 5:
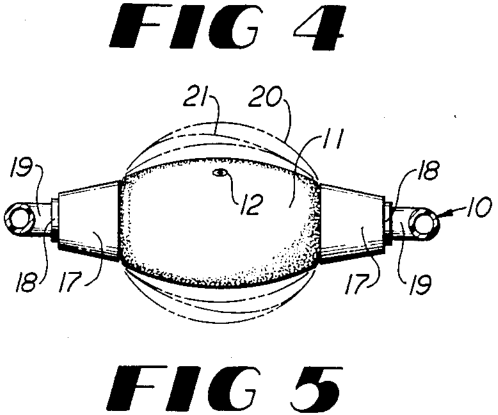
FIG. 5 is a similar section taken on line 5—5 of FIG. 3.

Another inherent feature or benefit derived from the manner in which the massage elements 11 are mounted on the device is that, during rotation, the massage elements tend to be self-aligning relative to the cups 17 on their parallel axes of rotation, which axes lie in the plane defined by the frame 10. The self-alignment ability of the oblate spheroids 11 is graphically depicted by the phantom lines 20 and 21, FIG. 5.

During use, the device is placed on a floor or other flat support surface and the user places his or her back on the device with the centers of the massage elements 11 under the spinal column. The massage elements yield somewhat and tend to flatten out against the spinal column and adjacent back muscles, and will generally conform to anatomical irregularities. The inflation pressure of the elements 11 can be adjusted to best suit the size, weight and comfort of the user while applying firm pressure on the spine.

The user grasps the opposite sides of the frame 10 with the hands at convenient points and uses the legs to propel the device back and forth longitudinally in a rolling mode on the floor. This action provides good exercise while simultaneously massaging the back muscles and spine vigorously from the base of the neck to the hips. It has been discovered that the oblate spheroidal shapes of the yielding massage elements 11 are the most ideal shapes possible to provide the desired back massage action. Spherical elements are uncomfortable and more nearly cylindrical elements are not capable of applying firm pressure to the spinal column.

In addition to being the ideal shape for back and spine massage, the oblate spheroid elements 11 possess the alreadydescribed advantages for easy mounting and removal from the holding cups 17 without the necessity for any additional mounting means, such as shafts extending entirely through the centers of the massage elements. The self-aligning ability of the elements 11 is another benefit arrived from their shapes.

While the massage elements or rollers 11 are shown as being of one size, in some cases, one or more of the massage rollers 11 may be of a larger or smaller size than the other massage rollers. This enables concentrating pressure on the spine and back muscles at one or more points with somewhat greater intensity than at other points. This feature, in conjunction with the variable inflatability of the rollers 11, renders the device highly versatile in its usage and enables it to be customized to the needs of particular users.

It is to be understood that the form of the invention herewith shown and described is to be taken as a preferred example of the same, and that various changes in the shape, size and arrangement of parts may be resorted to, without departing from the spirit of the invention or scope of the subjoined claims.

I claim:

1. A spinal massage and exercise device comprising a substantially flat frame, at least one yielding massage element on said frame and having the form of an oblate spheroid having tapered end portions and having its major axis extending across the frame in one direction, and hollow elements receiving said tapered end portions of said massage element and holding and supporting it rotatably on said frame, said hollow elements being frictionally and rotatably drivingly engaged with said tapered end portion whereby a user of the device may engage the spinal column and back muscles with the massage element near one side of the frame while grasping the frame with the hands while the massage element is rollingly engaging a substantially flat support surface.

2. A spinal massage and exercise device as defined in claim 1, and the massage element being a hollow inflatable element having an inflation valve whereby inflation pressure can be regulated.

3. A spinal massage and exercise device as defined in claim 1, and said hollow elements comprising cup elements receiving said tapered end portions in open ends thereof, rotary bushings secured to the cup elements, and shaft portions on said frame rotationally supporting said bushings.

4. A spinal massage and exercise device as defined in claim 1, and the device comprising a plurality of said yielding oblate spheroidal massage elements on said frame in substantially equidistantly spaced parallel relationship.

5. A spinal massage and exercise device as defined in claim 4, and said massage elements being hollow and inflatable and each having an inflation valve whereby the inflation pressure of each massage element can be independently regulated.

6. A spinal massage and exercise unit comprising a substantially rectangular frame, plural spaced parallel axis spinal massage rollers journaled within said frame between opposite sides thereof, said massage rollers being yielding and being formed as oblate spheroids whose exterior surfaces project substantially equidistantly beyond planes defined by opposite faces of said frame, the massage rollers including tapered end portions, and a pair of cup-like elements interengaged frictionally with said tapered end portions and being rotatably connected to the opposite sides of the frame between which the massage rollers extend and rotary bearing means connected between the cup-like elements and said frame.

7. A spinal massage and exercise unit as defined in claim 6, and the massage rollers comprising hollow inflatable rollers each having an inflation valve.

8. A spinal massage and exercise unit as defined in claim 7, and said means interengaged frictionally with said tapered end portions being tubular.

* * * * *